United States Patent
Chopra (10) Patent No.: US 8,292,917 B2
(45) Date of Patent: Oct. 23, 2012

(54) MEDICAL CLOSURE DEVICE

(75) Inventor: Gopal Chopra, San Francisco, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 336 days.

(21) Appl. No.: 11/960,641

(22) Filed: Dec. 19, 2007

(65) Prior Publication Data

US 2008/0097522 A1    Apr. 24, 2008

Related U.S. Application Data

(63) Continuation of application No. 10/636,791, filed on Aug. 7, 2003, now abandoned.

(51) Int. Cl.
*A61B 17/08* (2006.01)

(52) U.S. Cl. .................................................. 606/213

(58) Field of Classification Search ............ 606/213
See application file for complete search history.

(56) References Cited

U.S. PATENT DOCUMENTS

| | | | |
|---|---|---|---|
| 4,744,364 A | 5/1988 | Kensey | |
| 5,053,046 A | 10/1991 | Janese | |
| 5,254,133 A | 10/1993 | Scid | |
| 5,370,660 A | 12/1994 | Weinstein et al. | |
| 5,383,896 A | 1/1995 | Gershony et al. | |
| 5,441,517 A | 8/1995 | Kensey et al. | |
| 5,454,833 A | 10/1995 | Boussignac et al. | |
| 5,476,469 A | 12/1995 | Hathaway et al. | |
| 5,507,755 A | 4/1996 | Gresl et al. | |
| 5,531,759 A | 7/1996 | Kensey et al. | |
| 5,540,715 A | 7/1996 | Katsaros et al. | |
| 5,545,178 A * | 8/1996 | Kensey et al. | 606/213 |
| 5,601,602 A | 2/1997 | Powler | |
| 5,634,944 A | 6/1997 | Magram | |
| 5,643,317 A | 7/1997 | Pavcnik et al. | |
| 5,772,609 A | 6/1998 | Nguyen et al. | |
| 5,782,860 A | 7/1998 | Epstein et al. | |
| 5,810,884 A | 9/1998 | Kim | |
| 5,830,232 A | 11/1998 | Hasson | |
| 5,861,003 A | 1/1999 | Latson et al. | |
| 5,910,155 A | 6/1999 | Ratcliff et al. | |
| 5,984,948 A | 11/1999 | Hasson | |
| 6,004,341 A | 12/1999 | Zhu et al. | |
| 6,024,756 A * | 2/2000 | Huebsch et al. | 606/213 |
| 6,139,510 A | 10/2000 | Palermo | |
| 6,203,554 B1 | 3/2001 | Roberts | |
| 6,221,056 B1 | 4/2001 | Silverman | |

(Continued)

FOREIGN PATENT DOCUMENTS

WO        0200286       1/2002

(Continued)

*Primary Examiner* — Gary Jackson
*Assistant Examiner* — Diane Yabut
(74) *Attorney, Agent, or Firm* — Seager, Tufte & Wickhem, LLC (57) ABSTRACT

Several alternative designs, structures, assemblies, treatment methods and/or methods of manufacturing medical closure devices adapted and/or configured for closing an opening, for example, an incision or a puncture in the tissue of a patient, for example, the dural membrane of a patient. Some embodiments include a medical closure device including an elongated tubular member extending along a longitudinal axis. The tubular member including a distal section and a proximal section, and the distal section is expandable from a first configuration to a second expanded configuration through the application of a compressive force upon the distal section along the longitudinal axis.

20 Claims, 3 Drawing Sheets

U.S. PATENT DOCUMENTS

| | | |
|---|---|---|
| 6,283,984 B1 | 9/2001 | Ray |
| 6,312,446 B1 | 11/2001 | Huebsch et al. |
| 6,315,787 B1 | 11/2001 | Tsugita et al. |
| 6,334,865 B1 | 1/2002 | Redmond et al. |
| 6,482,235 B1 | 11/2002 | Lambrecht et al. |
| 6,531,147 B2 | 3/2003 | Sawhney et al. |
| 6,726,696 B1 * | 4/2004 | Houser et al. ............ 606/151 |
| 7,011,647 B2 | 3/2006 | Purdy et al. |
| 7,150,737 B2 | 12/2006 | Purdy et al. |
| 2003/0014016 A1 | 1/2003 | Purdy |
| 2003/0093105 A1 | 5/2003 | Huffmaster |
| 2003/0191496 A1 * | 10/2003 | Edwards et al. ............ 606/213 |

FOREIGN PATENT DOCUMENTS

| | | |
|---|---|---|
| WO | 0232320 | 4/2002 |

* cited by examiner

MEDICAL CLOSURE DEVICE

CROSS REFERENCE TO CO-PENDING APPLICATIONS

This application is a continuation of U.S. application Ser. No. 10/636,791, filed on Aug. 7, 2003, now abandoned, the entire disclosures of which are incorporated herein by reference.

TECHNICAL FIELD

The invention generally pertains to medical closure devices, such as medical devices for closing an opening in tissue bounding a cavity in the anatomy of a patient.

BACKGROUND

It is sometimes necessary in diagnosis and/or treatment of disease to gain access to, or navigate within certain anatomies of a patient. During such procedures, it is sometimes necessary to penetrate certain tissue that bounds a cavity in the anatomy of a patient. For example, certain treatment or operations require that an opening be created in tissue such as a membrane or vessel wall within the anatomy of the patient. For example, in some procedures, an opening, such as an incision or puncture, in created in the dural membrane of a patient to gain access to anatomies therein. The dural membrane covers the inside of the cranium and the spinal canal, and forms an enclosed system that contains other membranes, the brain, spinal cord, and Cerebrospinal fluid (C.S.F.).

After such procedures, it is often desirable to close the opening in the tissue. There are some known methods and devices for closing openings in tissue—each having advantages and disadvantages. There is an ongoing need to provide alternative designs, structures, assemblies, and/or treatment methods for closing an opening in the tissue of a patient, for example, the dural membrane of a patient.

SUMMARY OF SOME EMBODIMENTS

The invention provides several alternative designs, structures, assemblies, treatment methods and/or methods of manufacturing medical closure devices adapted and/or configured for closing an opening, for example, an incision or a puncture in the tissue of a patient, for example, the dural membrane of a patient.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME ILLUSTRATIVE EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. For example, although shown and discussed with specific reference to some embodiments which are adapted for use in closing an opening, such as an incision or puncture, in the dural membrane in the body of a patient, it should be understood that the invention may be adapted or configured for use in other portions of the anatomy. For example, certain aspects of the invention may be applicable for use in closing an opening in any tissue that bounds a cavity in the anatomy of a patient. For example, certain aspects of the invention may be applicable for use in closing tissue such as other anatomical tissues or membranes or walls within the anatomy, for example, within the vasculature, abdominal (i.e. to close an incision made during a laparascopy or laparotomy) or other portions of the anatomy.

An additional note with respect to the following description is that, while the closure device is described in terms of different sections, the device, or multiple sections thereof, may be made as a single element, for example, through extrusion, molding, casting, and the like. Variations in sizes and flexibility, as well as the inclusion of rigid or semi-rigid materials, should not be interpreted as requiring a certain method or type of construction. While the present description is written largely in terms of use in a human patient, the present invention may also be used with other organisms, for example in veterinary procedures by applying adaptations suited to a particular organism's anatomy.

Figure 1:
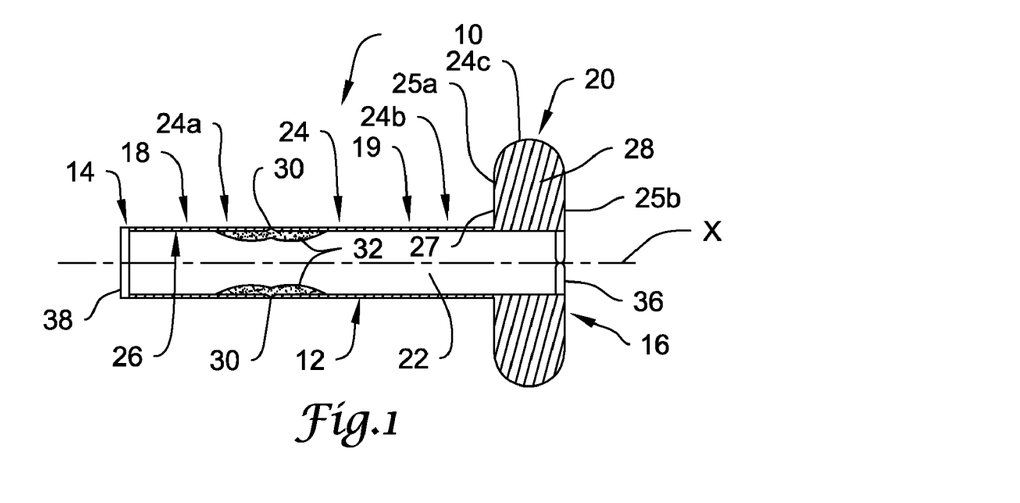
FIG. 1 is a schematic cross sectional side view of a closure device in a first, unexpanded configuration.

Refer now to FIG. 1, which is a diagrammatic cross sectional side view of one example embodiment of a closure device 10 adapted and/or configured for closing an opening in tissue bounding a cavity in the anatomy of a patient. In this embodiment, the device 10 includes a body member, such as an elongated tubular member 12 having a distal end 14 and a proximal end 16. The tubular member 12 includes a distal section 18 an intermediate section 19, and a proximal section 20, and defines an inner lumen 22 extending there through. The tubular member 12, and the inner lumen 22 defined thereby, extend generally along a longitudinal axis, X. In this document, the term "longitudinal" should be understood to mean in a direction corresponding to an elongated direction of the closure device 10. The tubular member 12 defines an outer surface 24 having an outer perimeter, and an inner surface 26 having an inner perimeter. The outer surface 24 includes a distal portion 24a corresponding to the distal section 18, an intermediate portion 24b corresponding to the intermediate section 19, and a proximal portion 24c corresponding to the proximal section 20. The distal end 14 of closure device 10 may be angled or tapered, or may be generally flat, as shown or otherwise adapted to facilitate insertion.

Although shown as including a generally circular cross section, tubular body member 12, proximal member 28, and the lumen 22, or portions of any of these, may include any of a broad variety of cross sectional shapes, often dependent upon the shape and size of the opening in the tissue to be closed or sealed, and/or upon the shape and size of other devices that may be used with the closure device 10. The structure, or portions thereof, may include any of a broad variety of cross-sectional shapes, for example, circle, oval, square, rectangle, or other polygon or like shapes, or combinations thereof. Additionally, although the sections 18, 19, and 20 and the lumen 22 are shown as including generally constant outer and inner diameters along the length thereof, in other embodiments, these diameters may change or taper along the length of each segment 18, 19, and 20 or along the length of the lumen 22.

In this embodiment, the device 10 also includes a first non-return valve 36 disposed in the lumen 22 at proximal end 16, and a second non-return valve 38 disposed in the lumen 22 at the distal end 14. The non-return valves 36 and 38 are adapted so that a needle, trochar, guidewire, catheter, or other such device or structure may be introduced through the valves 36 and 36 without allowing substantial fluid within the lumen of closure device to escape, and, conversely, without allowing foreign particles to enter the lumen 22 of closure device 10. For example, the non-return valve may be a hemostatic valve, membrane, or the like. In some embodiments, the non-return valves may be adapted and/or configured to include ports that can be accessed multiple times.

The proximal section 20 includes a proximal portion 28 disposed adjacent the proximal end 16 of the tubular member 12. The proximal portion 28 defines the outer surface portion 24c that has an outer perimeter. The intermediate section 19 of the tubular member defines outer surface portion 24b that has an outer perimeter, and the outer surface portion 24c has a greater outer perimeter than the outer surface portion 24b. In other words, the proximal portion 28 is bigger around than the intermediate section 32. Additionally, in the embodiment shown, the proximal portion 28 defines a distal side surface 25a and a proximal side surface 25b. The distal side surface 25a forms a stepped up or shoulder area 27 where the intermediate section 19 and proximal portion 28 meet. The proximal portion 28 can be a separate member that is attached or connected to the outer surface 24 of the of the tubular member 12 at the proximal section 20, or can be a widening or expansion in unitary construction with the tubular member 12 to created the increased outer perimeter. As will be discussed in more detail below, in at least some embodiments, the widened proximal portion 28 is adapted and/or configured such that the outer surface 24c has an outer perimeter that is larger than an outer perimeter of the opening in the tissue of the patient that is to be closed. As such, in at least some embodiments, the widened proximal portion 28 can be adapted and/or configured to acts as a stop and/or as a sealing portion that contacts the outer surface of the tissue in which the opening is being closed or sealed.

The intermediate section 19 of the tubular member 12 extends distally of the proximal portion 28, and as indicated above, includes an outer surface portion 24b that has an outer perimeter that is smaller than the outer perimeter of the proximal portion 28. The intermediate section 19 can be a separate member that is attached or connected to the proximal section 20, or can be of unitary construction with the proximal section 20. As will be discussed in more detail below, in at least some embodiments, the intermediate section 19 can have an outer surface 32 that has an outer perimeter that is sized and/or configured for insertion into the opening in the tissue to be closed or sealed. It can also have a length that is sized and/or configured to extend within the opening to be closed or sealed, and in some embodiments, at least the entire length of the opening to be closed or sealed. Therefore, in at least some embodiments, the intermediate section 19 is adapted and/or configured to extend within the opening in the tissue to be closed or sealed between the widened proximal portion 28 and the distal section 18.

The distal section 18 of the tubular member 12 extends distally of the intermediate section 19, and also includes an outer surface portion 24c that has an outer perimeter. The distal section 18 can be a separate member that is attached or connected to the intermediate section 19, or can be of unitary construction with the intermediate section 19. The distal section 20 includes at least a portion thereof that is adapted and/or configured to be radially expandable from a first configuration, wherein the outer surface portion 24c of the distal section 18 is sized for insertion into and through the opening in the tissue to be closed, to a second, radially expanded configuration, wherein at least a portion of the outer surface portion 24c of the distal section 18 has a larger outer perimeter than when in the first configuration. As such, the distal section 18 of the tubular member 12, when in the first, unexpanded configuration, is adapted and/or configured to be inserted through the opening in the tissue to be closed or sealed, and into the interior of the opening in the tissue. Thereafter, the distal section 18 can be expanded into the second, expanded configuration, wherein it can be adapted and/or configured to act as a stop and/or as a sealing portion that contacts the inner surface of the tissue in which the opening is being closed or sealed. In the embodiment of FIG. 1, the distal section 18 is shown in a first, or unexpanded configuration.

In some embodiments, the distal section 18 is configured such that the radial expansion of at least a portion of the distal section can be achieved through the application of sufficient compressive longitudinal force to the distal section 18. For example, in some embodiments, the distal section 18 includes at least one area 30 along the length thereof that has a reduced column strength relative to other portions of the distal section 18. Some embodiments may include multiple areas of reduced column strength. Such areas 30 of reduced column strength are adapted to bend or fold in an outward direction relative to the longitudinal axis, such that the outer surface 24a expands radially outward when a sufficient compressive longitudinal force is applied to the distal section 18. In other words, the area 30 has a weaker column strength than adjacent areas, and as such, it is adapted to give, and/or bend in an outward direction when the distal section 18 is placed under sufficient compressive force. This giving and/or bending in an outward direction resulting in radial outward expansion of at least a portion of the distal section 18 allows the distal section 18 to transition from the unexpanded to the expanded configuration.

The area 30 of reduced column strength can be achieved or created in any of a number of ways. For example, in the embodiment shown, the inner surface 26 of the distal section 18 includes a cylindrical portion having a reduced wall thickness to create the area 30 of reduced column strength. In other embodiments, an area of reduced column strength can be achieved through other means or mechanisms, for example, other structure, such as one or more groove, channel, furrow, notch, cut, fold, crease, wrinkle, ridge, kink, or other such structure defined in the wall of the distal section 18 that may result in reduced column strength, or a propensity to fold outwardly under compressive force. Additionally, an area 30 having reduced column strength or having a propensity to fold outwardly under compressive force may be created by using materials in such areas having different properties relative to the remainder of the distal section 18. For example, such an area may be created by using a material having a different modulus of elasticity from the remaining portions of the distal section 18. For example, such an area may include or be made of material having a reduced elastic modulus (i.e., increased flexibility) relative to other portions of the distal section 18, and would therefore have reduced column strength, and/or have a propensity to fold outwardly under compressive force.

Some embodiments may also include a binding mechanism to help maintain the distal section 18 in the expanded configuration. For example, in the embodiment shown, a binding material 32, such as an adhesive or other bonding agent or mechanism may be disposed on the inner surface 26 of the distal section 18. The binding material 32 may be disposed on either side, or on both sided of the area 30 such that when the area 30 of reduced column strength bends or folds in an outward direction, adjacent portions of the inner surface 26 about the fold can be bound together to help maintain the expanded configuration.

Figure 2:
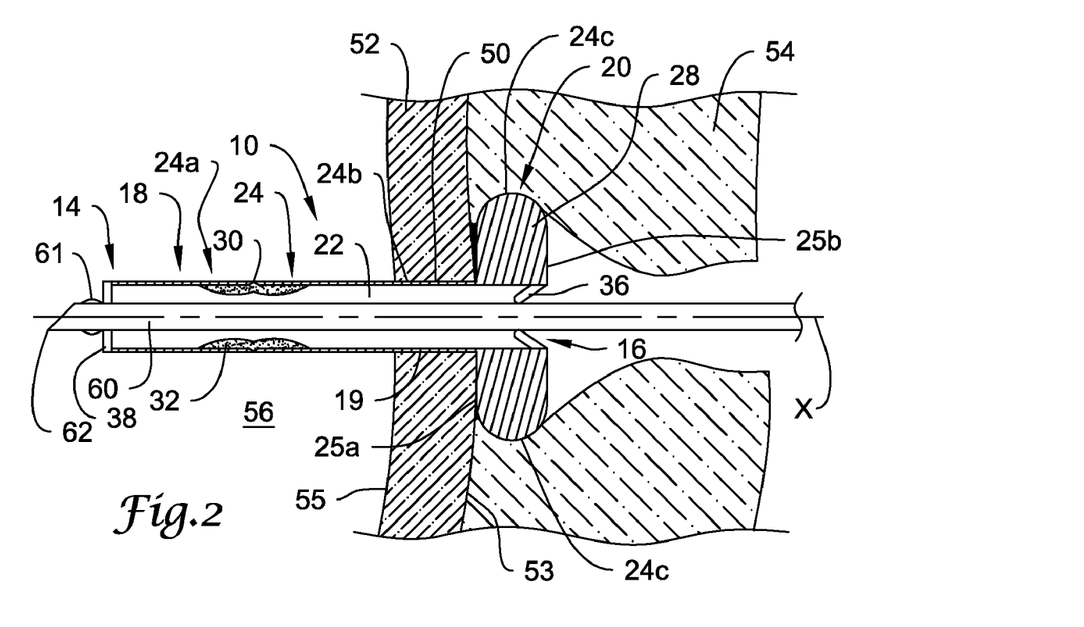
FIG. 2 is a schematic cross sectional side view of the closure device of FIG. 1, inserted into an opening in the dural membrane of an adult human being using an elongated insertion device.

Reference will now be made to FIGS. 2-4 for description of one example or use and/or operation of the example embodiment shown in FIG. 1. FIG. 2 is a diagrammatic side view of the closure device 10 of FIG. 1, in the unexpanded first configuration, inserted into an opening 50 in tissue 52 of a patient. For example, the opening 50 may be in the dural membrane 52 of a patient. The dural membrane 52 forms an enclosed system that contains other membranes, the brain, spinal cord, and Cerebrospinal fluid (C.S.F.). The dural membrane 52 is located beneath other tissue 54, and encloses and defines a cavity 56, for example, the subarachnoid space of a patient. As shown, the dural membrane 52 includes an outer surface 53 and an inner surface 55. Some examples of procedures and devices that involve creating an opening in the dural membrane are disclosed copending U.S. patent application Ser. Nos. 10/328,560 filed on Dec. 23, 2002, entitled METHODS AND APPARATUSES FOR NAVIGATING THE SUB-ARACHNOID SPACE; 09/905,670 filed on Jul. 13, 2001, entitled METHODS AND APPARATUSES FOR NAVIGATING THE SUBARACHNOID SPACE; 10/328,349 filed on Dec. 23, 2002, entitled INTRODUCER SHEATH; and 10/328,373, filed on Dec. 23, 2002, entitled GUIDE CATHETER FOR INTRODUCTION INTO THE SUBARACHNOID SPACE AND METHODS OF USE THEREOF, all of which are incorporated herein by reference.

The closure device 10 is shown inserted through the tissue 54 above the dural membrane 52, and into the opening 50. The distal section 18 and the intermediate section 19 are sized to extend through or within the opening 50, while the widened proximal portion 28 is adapted and/or configured such that the outer surface 24c has an outer perimeter that is larger than an outer perimeter of the opening 50. The distal section 18 is shown in the unexpanded first configuration extending into the subarachnoid space 56. The intermediate section 19 is shown as extending within the opening 50. The proximal section 20, including proximal portion 28, is shown on the outside, or proximal side, of the opening 50. The distal side surface 25a of the widened proximal portion 28 makes contact with the outer surface 53 of the dural membrane 52 about the opening 50.

The closure device 10 can be inserted into the opening 50 using any suitable device or mechanism. For example, an insertion device, such as a needle 60, trochar, or the like, can be disposed into the lumen 22 of the device 10. The needle 60, or other device, can then be used to insert the closure device 10 into the opening 50, and the device 10 can be advanced into the opening 50 until the widened proximal portion 28 makes contact with the outer surface 53 of the dural membrane 52. In some embodiments, the needle 60 may be inserted through both of the non-return valves 36 and 38, which can be adapted to provide a frictional fit with the needle 60 such that insertion can be made with relatively little or no movement of the device 10 relative to the needle 60. In some embodiments, the needle 60 or other insertion device can be adapted or configured to include properties or structures that facilitate insertion and/or cooperation with the device 10. For example, some embodiments may include a tapered or sharpened distal tip 62 to facilitate insertion, or protrusions 61 on the outer surface thereof that are adapted to create or provide additional frictional fit or engagement with the valves 36 and 38.

Although depicted as being inserted with a needle 60, the device can be inserted into the opening 50 using any suitable insertion instrument, technique or apparatus. For example, in other examples, a guidewire, catheter, or the like, may be disposed such that it extends through the opening 50 in the dural membrane 52 and into subarachnoid space 56, and may be used to guide or facilitate the introduction of closure device 10.

Figure 3:
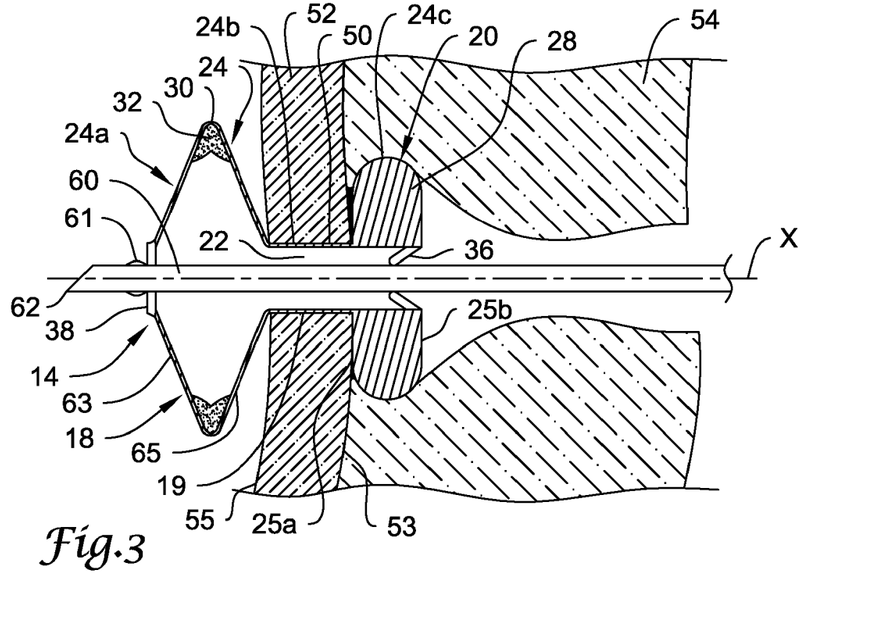
FIG. 3 is a schematic cross sectional side view of the closure device of FIG. 2, wherein the distal portion of the closure device is being engaged by the insertion device such that it is partially expanded.

Refer now to FIG. 3, wherein the distal section 18 is shown in a partially expanded configuration, in transition between the unexpanded configuration, and a fully expanded configuration. Once the device 10 is inserted into the opening 50, as shown in FIG. 2, the needle 60 can begin to be withdrawn, as shown in FIG. 3, for example, along longitudinal axis X. In some embodiments, it may be necessary during withdrawal of the needle 60 to apply pressure to the widened proximal portion 28 such that it maintains a desired position, for example, in contact with the outer surface 53 of the dural membrane 52 about the opening 50.

During withdrawal of the needle 60, the needle 60 can engage structure in the distal section 18 of the tubular member 12. For example, in the embodiment shown, the needle 60, through friction, engages the distal non-return valve 38. The protrusions 61 on the needle 60 can aid in the frictional engagement of the distal non-return valve 38, or may in some embodiments provide for an interference fit with the distal non-return valve 38. As the needle 60 is withdrawn, a compressive longitudinal force is applied to the walls of the tubular member 12 due to the frictional or interference engagement of the needle 60 with the distal non-return valve 38. The compressive longitudinal force is sufficient to cause the areas 30 of reduced column strength on the distal section 18 to bend or fold in an outward direction relative to the longitudinal axis X. As the bend or fold is created, the outer surface 24a expands radially outward. In the embodiment shown in FIG. 3, the longitudinal force and the bending and/or folding of the distal section 18 about the area 30 creates a proximal region or fold 65 in the distal section 18 that is pulled toward the inner surface 55 of the dural membrane 52. Additionally, a distal region or fold 63 in the distal section 18 is created, and the distal region 63 is pulled toward the proximal region 65.

Figure 4:
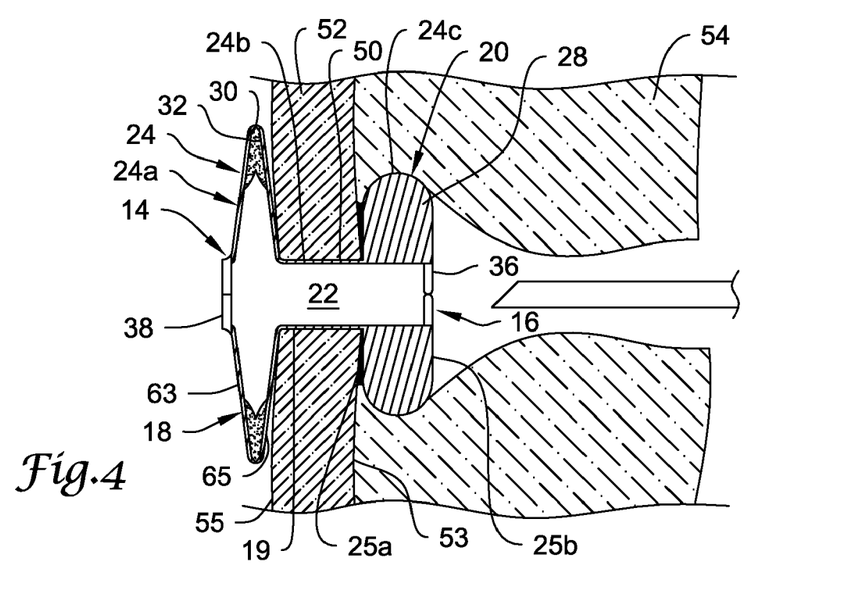
FIG. 4 is a schematic cross sectional side view of a the closure device of FIG. 3, wherein the distal portion of the closure device has been fully expanded to close the opening in the dural membrane.

Refer now to FIG. 4, wherein the distal section 18 is shown in a fully expanded configuration. In this fully expanded configuration, at least a portion of the proximal region or fold 65 in the distal section 18 is pulled against the inner surface 55 of the dural membrane 52. Additionally, the distal region or fold 63 is pulled toward the proximal region 65, and the adhesive material 32 can act to bind the two regions 63 and 65 together to help maintain the expanded configuration. The outer surface 24a of the distal region has expanded radially outward such that it has an outer perimeter that is greater than the outer perimeter of the opening 50 in the dural membrane 52. As such, the opening 50 has been closed by the closure device 10. The closure device is maintained in position by the radially expanded distal section engaging the inner surface 55 of the dural membrane, and the widened proximal portion 28 engaging the outer surface 53 of the dural membrane 52 about the opening 50. The intermediate section 19 extends through the opening, and interconnects the distal section 18 and the proximal portion 28. When in place, and the distal section is in the expanded configuration, the closure device 10 acts to at least substantially close or seal the opening 50.

In some other embodiments, it is also contemplated that a binding mechanism, such as an adhesive type material, may be used on the outer surface 24a of the distal section 18. For example, an adhesive material could be included on the outer surface of the proximal region 65 of the distal section 18. At least a portion of the outer surface of this region 65 may come into contact with the inner surface 55 of the dural membrane, and an adhesive material applied thereto could provide for a bond between the proximal region 65 and the inner surface 55 of the dural membrane. Such a bond may help maintain the closure device 10 in the expanded configuration, and may additionally help to seal the opening. Additionally, in some embodiments, a binding mechanism, such as an adhesive type material, may be used on an outer surface of the proximal portion 28. For example, an adhesive material may be applied to the distal side surface 25a and could provide for a bond between the proximal portion 28 and the outer surface 53 of the dural membrane. Such a bond may help maintain the closure device 10 in position relative to the opening, and may additionally help to seal the opening 50. It is contemplated that in at least some such embodiments, the adhesive material used would be compatible with the tissue or anatomy in which it is being used.

Additionally, in some embodiments, when the closure device 10 is in place within the anatomy, it can be used as a port for introduction of other devices and/or structures. For example, with the closure device 10 in place, in some embodiments, additional structures may be introduced into the cavity defined by the tissue, (such as the subarachnoid space in the case of the dural membrane), through the lumen 22 within the closure device 10. For example, a guidewire, catheter, introducer sheath, needle, trochar, endoscopes, flush tubes, and other devices, or the like, may be advanced through the lumen 22 via the valves 36 and 38 and into the cavity 56. Such additional devices may then be navigated or advanced within the cavity 56, or may take samples of fluid, such as CSF, or may introduce material, such as drugs, marker fluid, or the like, into the cavity 56. The closure device 10, including for example the non-return valves 36 and 38 may be adapted and/or configured to be accessed multiple times by one or more devices, and in some examples, can remain in place for a period of time to act as an access port to the anatomy. Additionally, while the embodiments shown include a single lumen 22, other embodiments may include multiple lumens. Such an embodiment can be, for example, adapted for use with or introduction of multiple devices, such as guidewires, catheters and the like, through the separate lumens.

Additionally, the closure device 10 may act as a platform for additional structures or devices. For example, the distal section 18 may include a transducer, for example, a microsensor embedded into a wall of the closure device 10 for sensing the temperature, pressure, body chemistry or the like inside the cavity 56, such as the subarachnoid space, or other anatomy in which the device 10 is used. Such a transducer may be coupled to an electric (i.e. a wire) or optic connection running along, through, or embedded into the tubular member 12 from a distal location to a proximal location. In other embodiments, such a transducer may be a wireless sensor, for example, a wireless resonant pressure or temperature sensor. The transducer may be included for determining a physiologic property during an operation, or to assist in diagnosis. Any of a wide variety of small sensing devices may be used as a transducer including, for example, resonant sensors, micromachined sensors, or even more conventional sensors which, though relatively bulky, may be incorporated into or attached to the closure device 10.

The size and dimensions of the closure device 10, and/or components or segments thereof, is greatly dependent upon the size and dimensions of the particular anatomy in which it is intended for use, and the size of the opening in the anatomy that is being closed. Thus, the lengths and diameters of different segments of the closure device 10 may thus be adapted for particular usages, and can vary greatly. For example, the outer diameter and length of the intermediate section 19 and the distal section 18 in the unexpanded configuration may be adapted for entry into a particular opening size in a particular anatomy, as the allowed outer diameters and length available and necessary for entry may vary from one particular opening size and anatomy to the next, as well as from one patient to the next. Likewise, the length and outer diameter of the proximal section, including the proximal portion 28, and the distal section 18 in an expanded configuration may also vary greatly, depending upon the size of the opening to be closed, and the available space in the anatomy. In some example embodiments, the device can have dimensions that are particularly adapted and/or configured for closing an opening in the dural membrane. Additionally, the dimensions of the lumen 22 and of the non-return valves 36 and 38 may vary greatly, depending upon the dimensions of the other components or sections, and upon the dimensions of other devices, if any, that are intended for use with the device.

With respect to the proximal section 20, it is possible to have an even larger lumen 22 within that section to make the lumen more easily accessed and/or passed. For example, because the proximal section 20 is not inserted into the opening 50 the outer diameter of the proximal section 20 is not as subject to the anatomical limits of a patient into whom the device is inserted, and hence there are fewer limits on the inner lumen 22 diameter in the proximal section 20, either.

A wide variety of materials may be used to make the closure device 10, or sections or portions thereof. For example, the closure device 10, including the tubular body member 12, the proximal member 28, or portions thereof, can be manufactured from any suitable material to impart the desired characteristics. Some examples of suitable materials can include, for example, polymers, metal-polymer composites, metals, metal alloys, or the like, or combinations or mixtures thereof. Examples of some suitable materials include, but are not limited to, polymers such as polyoxymethylene, polybutylene terephthalate, polyether block ester, polyether block amide, fluorinated ethylene propylene, polyethylene, polypropylene, polyvinylchloride, polyurethane, polytetrafluoroethylene (PTFE), polyether-ether ketone, polyimide, polyamide, polyphenylene sulfide, polyphenylene oxide, polysulfone, nylon, perfluoro(propyl vinyl ether), polyether-ester, polymer/metal composites, etc., or mixtures, blends or combinations thereof. One example of a suitable polyether block ester is available under the trade name ARNITEL, and one suitable example of a polyether block amide is available under the trade name PEBAX®, from ATOMCHEM POLYMERS, Birdsboro, Pa. In some embodiments, the polymer material of certain sections of the closure device 10 can be blended with a liquid crystal polymer (LCP). For example, the mixture can contain up to about 5% LCP. This has been found to enhance torqueability in some embodiments.

Some examples of suitable metals and metal alloys include nickel-titanium alloy, such as linear elastic or superelastic nitinol, nickel-chromium alloy, nickel-chromium-iron alloy, cobalt alloy, stainless steel, such as 304v stainless steel; or the like; or other suitable material.

The closure device 10, for example the tubular body member 12 and the proximal member 28, can be made of unitary construction, or can be made up of a plurality of tubular segments coupled together, each segment being made of materials having the same or different properties. For example, in some embodiments, different portions or sections of the device 10 can include or be made of materials, or have structure that renders them more flexible or softer than other portions of the device 10. For example, in some embodiments, the distal section 18 may be more flexible or softer than at least a part of the intermediate or proximal sections 19 and 20. Likewise, in some embodiments, the distal section 18 can be less flexible or harder than at least a part of the of the intermediate or proximal sections 19 and 20. These are only a couple of examples, but it should be understood that variances in the characteristics of the different sections can be achieved as desired.

It can be appreciated that the closure device 10 can be made of a single layer of material, or a plurality of layers. For example, the tubular body member 12 and the proximal member 28, can include one or more layers disposed or stacked on top of one another. The different layers may be made of the same material or different materials. In one example, one of the layers may be made of a generally less flexible polymer than the other(s). In another example, one or more of the layers may be made of or doped with an indicator material to enhance imaging. Additionally, in some embodiments, one of the layers may act as a support layer, and can include, for example, support structure, such as a braid, coil, or other such structures. The closure device 10, including the tubular body member 12 and the proximal member 28 can be constructed using any appropriate technique, for example, by extrusion, a heat bonding process, casting, molding, and the like.

In some embodiments, the device 10 may be provided with an initial rigid shape, but may be re-shaped by a physician before insertion to better match the anatomy of the patient. For example, the distal section 18, intermediate section 19, and/or proximal section 20, or portions thereof, may be made of a material such as PTFE that is rigid, but may be heated and re-shaped, so that once re-cooled, the distal section, intermediate section 18, and/or proximal section 20 will retain the new shape.

In some embodiments, the closure device, or portions thereof can be made of or include a lubricious material, for example tetrafluoroethylene, or a copolymer of tetrafluoroethylene with perfluoroalkyl vinyl ether (more specifically, perfluoropropyl vinyl ether or perfluoromethyl vinyl ether), or the like. Also, in some embodiments, the closure device, or sections or portions thereof can include a coating, for example a lubricious, a hydrophilic, a protective, or other type of coating may be applied over portions or all of the device 10, or within the lumen 22 of the device. Hydrophobic coatings such as fluoropolymers provide a dry lubricity which can improve insertion, and when disposed in the lumen 22, and improve insertions of other devices therethrough. Lubricious coatings can also aid in this manner. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The distal section 18 (as well as the rest of closure device 10, as desired) may also include one or more markers or a coating to enhance its imaging visibility, for example MRI visibility, and, for some embodiments, may include radiopaque materials or other high visibility materials adapted for use with other imaging technologies, such as fluoroscopy. For some embodiments suggested herein, the closure device may be made of material and structure compatible with certain imaging techniques, for example an MRI scanning compatible material or structure. For example, ferrous materials, such as some stainless steel alloys often used to provide braided reinforcement to catheters, are typically magnetically responsive, and are generally not used in conjunction with MRI equipment, or are provided with structure that would render them compatible with MRI equipment. However, other embodiments, may not include materials that are currently MRI compatible.

Figure 5:
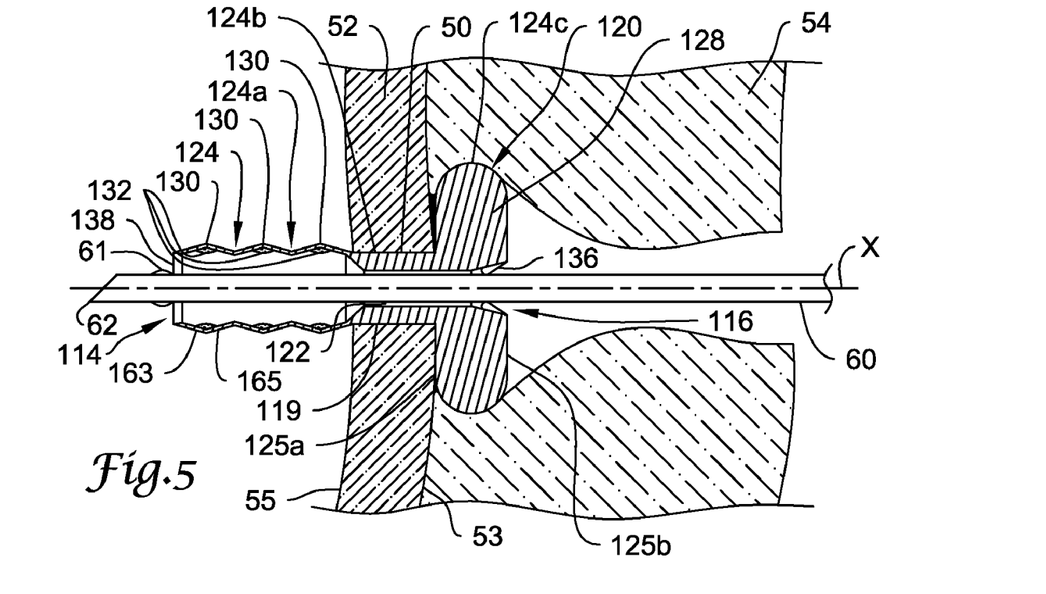
FIG. 5 is a schematic cross sectional side view of an alternative embodiment of a closure device in a first, unexpanded configuration.

Refer now to FIG. 5 which is a side view of another illustrative embodiment showing a closure device 110, this time including some alterations to the tubular member 112. In this embodiment, the device 110 also includes a body member, such as an elongated tubular member 112 having a distal end 114 and a proximal end 116. The tubular member 112 includes a distal section 118 an intermediate section 119, and a proximal section 120, and defines an inner lumen 122 extending there through. The tubular member 112, and the inner lumen 122 defined thereby, extend generally along a longitudinal axis, X. Likewise, the tubular member 112 defines an outer surface 124 having an outer perimeter, and an inner surface 126 having an inner perimeter. The outer surface 124 includes a distal portion 124a corresponding to the distal section 118, an intermediate portion 124b corresponding to the intermediate section 119, and a proximal portion 124c corresponding to the proximal section 120. Similar to the embodiment discussed above, the device 110 also includes a first non-return valve 136 disposed in the lumen 122 at proximal end 116, and a second non-return valve 138 disposed in the lumen 122 at the distal end 114.

The proximal section 120 and intermediate section 119 are configured substantially similar to the proximal section 20 and intermediate section 19 embodiment shown in FIG. 1-4. For example, the proximal section 120 includes a proximal portion 128 defining the outer surface portion 24c that has an outer perimeter that is greater than the outer perimeter of outer surface portion 24b. Additionally, the proximal portion 128 defines a distal side surface 125a and a proximal side surface 125b, and a stepped up or shoulder area 127.

However, the distal segment 118 in this embodiment includes a plurality of areas 130 along the length thereof that have a reduced column strength relative to other portions of the distal section 118. Such areas 130 of reduced column strength are adapted to bend or fold in an outward direction relative to the longitudinal axis, such that the outer surface 124a expands radially outward when a sufficient compressive longitudinal force is applied to the distal section 118. This giving and/or bending in an outward direction resulting in radial outward expansion of at least a portion of the distal section 118 allows the distal section 118 to transition from an unexpanded to an expanded configuration. In this embodiment, the areas 130 of reduced column strength are created by reducing the wall thickness on a portion of the inner surface 126 of the distal section 118.

In FIG. 5, the closure device 110 has been inserted into an opening 50 in tissue 52 of a patient, for example, an opening 50 in the dural membrane 52 of a patient. A needle 60 was used for insertion, and the needle 60 is being withdrawn, such that the distal section 118 is in a partially expanded configuration. During withdrawal, the needle 60, engages the distal non-return valve 138, and a compressive longitudinal force is applied to the walls of the tubular member 112. The compressive longitudinal force is sufficient to cause the areas 130 of reduced column strength to bend or fold in an outward direction relative to the longitudinal axis X. As the bends or folds are created, the outer surface 24a expands radially outward. In the embodiment shown in FIG. 5, the longitudinal force and the bending and/or folding of the distal section 118 about the areas 30 creates a plurality of folds 165, each fold 165 being proximal to an adjacent area 130. The folds 165 are pulled in a proximal direction. The proximal—most fold 165 is pulled toward the inner surface 55 of the dural membrane 52. Additionally, the longitudinal force creates a plurality of folds 163, each fold 163 being distal to an adjacent area 130. Each of the folds 163 is pulled toward the associated proximal fold 165 about the areas 130.

Figure 6:
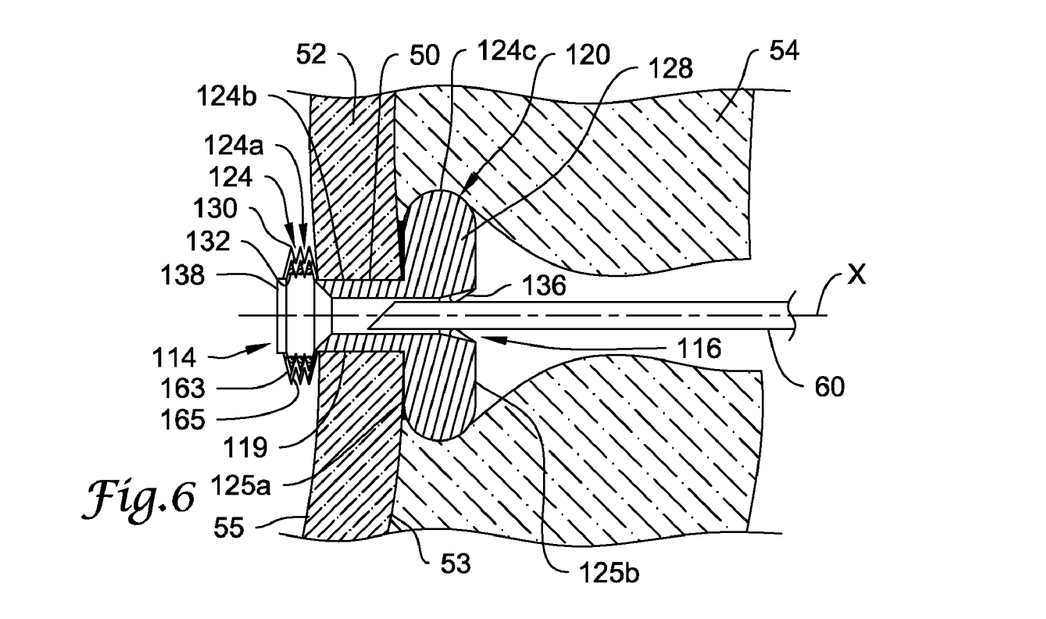
FIG. 6 is a schematic cross sectional side view of the closure device of FIG. 5, wherein the distal portion of the closure device has been fully expanded to close the opening in the dural membrane.

Refer now to FIG. 6, wherein the distal section 118 is shown in a fully expanded configuration. In this fully expanded configuration, at least a portion of the most proximal fold 165 is pulled against the inner surface 55 of the dural membrane 52. Additionally, each of the folds 163 is pulled toward the associated folds 165 about each of the areas 130. An adhesive material 132 can act to bind each of the two folds 163 and 165 together to help maintain the expanded configuration. The outer surface 124a of the distal region 118 has expanded radially outward such that it has an outer perimeter that is greater than the outer perimeter of the opening 50 in the dural membrane 52. As such, the opening 50 has been closed by the closure device 110. The closure device is maintained in position by the radially expanded distal section 118 engaging the inner surface 55 of the dural membrane, and the widened proximal portion 128 engaging the outer surface 53 of the dural membrane 52 about the opening 50. The intermediate section 119 extends through the opening 50, and interconnects the distal section 118 and the proximal portion 128. When in place, and the distal section 118 is in the expanded configuration, the closure device 110 acts to at least substantially close or seal the opening 50.

The present invention should not be considered limited to the particular examples described above, but rather should be understood to cover all aspects of the invention as fairly set out in the attached claims. For example, as discussed above, it should be understood that other embodiments of such devices can be adapted and/or configured for use in portions of the anatomy other than the dural membrane to close or seal an opening in other tissue. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What is claimed is:

1. A medical device for closing an opening in a tissue in a body of a patient, the device comprising:
    an elongated tubular member extending along a longitudinal axis, the elongated tubular member including a distal section and a proximal section, wherein the distal section is radially expandable from a first configuration to a second expanded configuration through an application of a compressive force upon the distal section along the longitudinal axis;
    wherein the proximal section defines an outer surface and includes a widened proximal portion member attached to the outer surface of the proximal section;
    a binding material including an adhesive disposed on an interior surface of the elongate tubular member in the distal section, wherein the binding material is configured to maintain the distal section in the second expanded configuration after the distal section is radially expanded from the first configuration to the second expanded configuration;
    wherein the elongated tubular member is adapted to permit an insertion device to extend through the elongated tubular member and extend distally therefrom such that withdrawing the insertion device applies the compressive force; and
    a first non-return valve disposed within the proximal section.

2. The medical device of claim 1, wherein the distal section includes a plurality of portions, and at least one of the portions has a reduced column strength relative to other portions of the distal section.

3. The medical device of claim 2, wherein the portion of reduced column strength is configured to create an outwardly extending bend or fold in the distal portion relative to the longitudinal axis when the compressive force is applied to the distal section.

4. The medical device of claim 3, wherein the distal section defines an outer surface, and the outwardly extending bend or fold in the distal portion expands the outer perimeter of at least a portion of the outer surface of the distal section.

5. The medical device of claim 1, wherein the distal section defines an outer surface, and when the distal section is in the first configuration, the outer surface of the distal section has a first sized outer perimeter, and when the distal section is in the second configuration, the outer surface of the distal section has a second sized outer perimeter greater than the first sized outer perimeter.

6. The medical device of claim 1, wherein the distal section defines an outer surface, and when the distal section is in the first configuration, the outer surface of the distal section is sized to have an outer perimeter that is adapted for insertion through the opening in the tissue in the body of the patient, and when the distal section is in the second configuration, at least a portion of the outer surface of the distal section is expanded in size to have an outer perimeter that is greater than when in the first configuration.

7. The medical device of claim 6, wherein when the distal section is in the second configuration, at least a portion of the outer surface of the distal section is expanded in size to have an outer perimeter that is greater than an outer perimeter of the opening in the tissue in the body of the patient.

8. The medical device of claim 1, wherein the widened proximal portion member defines an outer surface having an outer perimeter that is greater than an outer perimeter of the opening in the tissue in the body of the patient.

9. The medical device of claim 1, wherein the elongated tubular member further includes an intermediate section connecting the distal section and the proximal section.

10. The medical device of claim 9, wherein the intermediate section is configured to extend within the opening in the body of the patient between the distal section and the proximal section.

11. The medical device of claim 10, wherein the tissue in the body of the patient includes an inner surface and an outer surface, and the device is configured such that when the device is inserted into the opening to close the opening, the proximal section is configured to contact the outer surface of the tissue, and the distal section, when in the second expanded configuration, is configured to contact the inner surface of the tissue.

12. The medical device or claim 1, wherein the opening in the tissue in the body of the patient comprises an opening in the dural membrane of the patient.

13. A medical device for closing an opening in a dural membrane of a patient, the device comprising:
  a tubular proximal section defining an outer surface having an outer perimeter;
  a tubular intermediate section connected to the proximal section, the intermediate section defining an outer surface having an outer perimeter that is less than the outer perimeter of the proximal section;
  a tubular distal section connected to the intermediate section, the distal section being configured to be radially expandable from a first configuration to a second expanded configuration through an application of a compressive force upon the distal section, the distal section being adapted to permit an insertion device to extend therethrough such that withdrawing the insertion device applies the compressive force;
  a bonding agent disposed on an interior surface of the tubular distal section, wherein the bonding agent is configured to maintain the tubular distal section in the second expanded configuration after the tubular distal section is radially expanded from the first configuration to the second expanded configuration; and
  a non-return valve disposed within the tubular distal section.

14. The medical device of claim 13, wherein the tubular proximal section is configured to contact the outer surface of the dural membrane, the tubular intermediate section is configured to extend within the opening in the dural membrane between the tubular proximal section and the tubular distal section, and the tubular distal section, when in the first configuration, is adapted for insertion through the opening in the dural membrane, and when in the second configuration, is configured to contact the inner surface of the dural membrane.

15. The medical device of claim 13, wherein the outer perimeter of the tubular proximal section is configured to be greater than an outer perimeter of the opening in the dural membrane.

16. The medical device of claim 13, wherein a tubular distal section is configured to be inserted through the opening in the dural membrane when in the first configuration, and is adapted to expand and close the opening when in the second, expanded configuration.

17. The medical device of claim 13, wherein the tubular intermediate section is configured to extend within the opening in the dural membrane.

18. The medical device of claim 13, wherein the tubular distal section includes a plurality of portions, and at least one of the portions has a reduced column strength relative to other portions of the tubular distal section.

19. The medical device of claim 18, wherein the at least one of the portions of reduced column strength is configured to create an outwardly extending bend or fold in the tubular distal portion relative to the longitudinal axis when the compressive force is applied to the tubular distal section.

20. The medical device of claim 19, wherein the tubular distal section defines an outer surface, and the outwardly extending bend or fold in the tubular distal portion expands the outer perimeter of at least a portion of the outer surface of the tubular distal section.

* * * * *